United States Patent [19]

Kudo

[11] 4,284,357
[45] Aug. 18, 1981

[54] DEVICE FOR CONTINUOUSLY INSPECTING A SURFACE

[75] Inventor: Hisashi Kudo, Fujinomiya, Japan

[73] Assignee: Fuji Photo Film Co., Ltd., Minami-ashigara, Japan

[21] Appl. No.: 104,950

[22] Filed: Dec. 18, 1979

[30] Foreign Application Priority Data

Dec. 27, 1978 [JP] Japan ............................. 53/159963

[51] Int. Cl.³ ........................................ G01N 21/86
[52] U.S. Cl. .................................. 356/431; 258/563
[58] Field of Search ..................... 356/431, 429, 381; 250/563, 562, 548

[56] References Cited

U.S. PATENT DOCUMENTS 1,963,128  6/1934  Geister .............................. 356/381
3,618,063  11/1971 Johnson ............................ 356/431

FOREIGN PATENT DOCUMENTS 784144 10/1957 United Kingdom ................. 356/335

Primary Examiner—John K. Corbin
Assistant Examiner—Bruce Y. Arnold
Attorney, Agent, or Firm—Sughrue, Mion, Zinn, Macpeak and Seas

[57] ABSTRACT

A device for inspecting the surface of an article such as a moving paper web by scanning a bent surface of the object tangentially with a laser light beam. The scanned beam is received and converted into an electrical signal in which peaks therein above a pre-set level represent defects in the object. A servo feedback circuit is disclosed for maintaining the position of the scanning beam constant with respect to the inspected surface of the object despite variations in the position of the mechanism conveying the object.

9 Claims, 5 Drawing Figures

DEVICE FOR CONTINUOUSLY INSPECTING A SURFACE

BACKGROUND OF THE INVENTION

The present invention relates to a device for continuously inspecting surface conditions such as the surface smoothness of a belt-like article which is long and wide. More particularly, the invention relates to a device for quantitatively inspecting and measuring variations in the smoothness of the surface of a belt-like article such as a high-quality coated paper whose surface flatness must be accurately and precisely monitored so that the surface smoothness is maintained within an allowable range.

In general, a process of manufacturing high-quality coated papers or the like must be strictly controlled. However, in the course of manufacturing such articles, it is difficult to completely prevent defects from occurring such as the occurrence of defects in the form of projections which are due to relatively large particles contained in the surface coating material. Accordingly, it is essential to check for the occurrence of such defects at all times in order to be able to remove the defective articles.

In a conventional method for continuously inspecting the surface of an elongated article of the type described above, in general, foreign matter or projections are detected from the vertical movement of a roll provided on a lever arm which precisely follows the surface of the article. However, such a method utilizing a contact system is disadvantageous in the following points. The measurement accuracy varies greatly with the speed of an object or an article to be inspected. Secondly, whenever an object or an article to be inspected is different in thickness, an adjustment of the inspecting apparatus is quite troublesome. Furthermore, when foreign matter or a protrusion is detected, the article may be scratched. That is, secondary damage may be inflicted on the article and at worst the article may be deformed or torn.

On the other hand, a method of monitoring the surface of an article for unevenness and scratches has been employed which utilizes an optical system in which no roll is brought into contact with the object to be inspected. Such a system has been employed for inspecting, for instance, oil packages which are used for the brake system in an automobile. (See, for example, Japanese Laid-Open Patent Application No. 99360/1975.) If such an optical system is employed, the disadvantages accompanying the above-described method utilizing a contact system can be eliminated. However, such a system which is capable of operating with a belt-like article has been herebefore unknown.

SUMMARY OF THE INVENTION

Accordingly, an object of this invention is to provide a device for continuously inspecting a surface in which an optical system is utilized as means for inspecting the surface of a belt-like article in which the scanning speed of an inspecting light beam in the widthwise direction of the article to be inspected is varied in association with the speed of the object, and foreign matter or projections on the surface of the article are detected whenever their size is outside an allowable range so as to permit the operation of a check mechanism.

Provided in accordance with the invention is a device for continuously inspecting a surface which includes a cylindrical roll for curving and conveying an object to be inspected, a light emitting unit for emitting a light beam tangential to the curved surface including the upper surface of the object on the cylindrical roll with the beam scanned in the direction of the width of the object, and a light receiving unit for receiving the light beam for detecting variations in the intensity of the light beam there received by comparing the intensity of the received beam with a reference signal. In a preferred embodiment, the reference signal is produced by diverting a portion of the light beam before it reaches the scanned surface. A circuit for correcting the beam path position for changes in the gross position of the object and cylindrical roll may be provided.

BRIEF DESCRIPTION OF THE DRAWINGS

This invention will be described with reference to its embodiments shown in the accompanying drawings in which.

DESCRIPTION OF THE PREFERRED EMBODIMENTS

Figure 1:
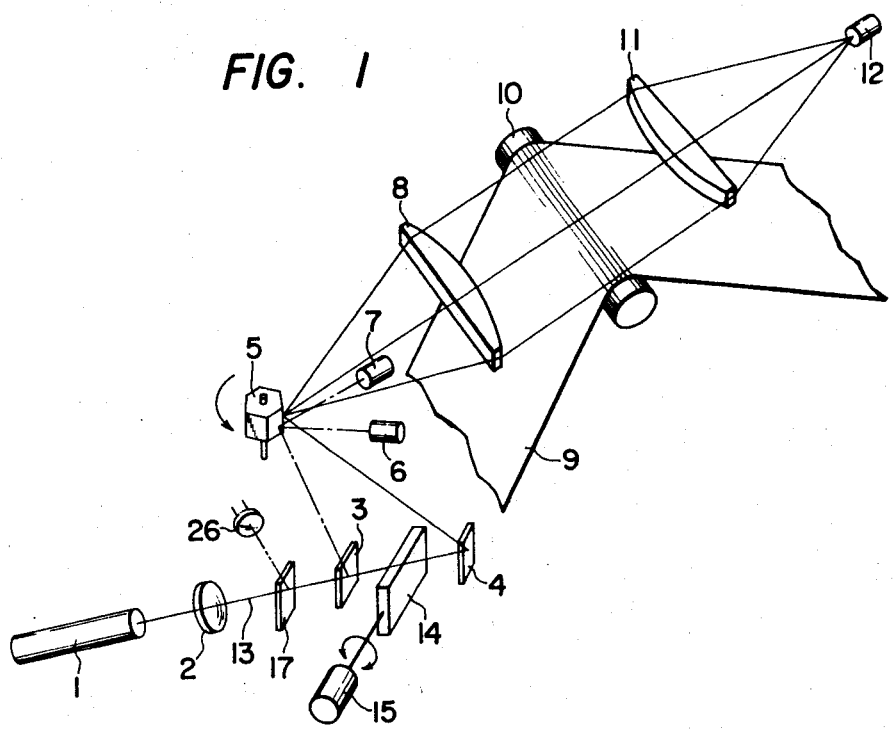
FIG. 1 is a perspective view showing a first embodiment of a surface inspecting apparatus according to the invention.

An apparatus for continuously inspecting a surface according to the invention is shown in FIG. 1 in a perspective view. An object 9 to be inspected is conveyed along a path which includes a bent portion around the surface of a conveying roller 10. A laser beam 13 emitted from a laser source 1 passes through a lens system which is arranged to form a focal point with a predetermined preferred cross-section at an inspection position located in the direction tangential to the curved upper surface of the object 9. More specifically, the emitted laser beam passes through a condenser lens 2 and half-silvered mirrors 17 and 3. The half-silvered mirror 17 is here used generically to refer to any device which is suitable for splitting the light beam into two portions, one of which is measured by photodiode 26, and the other of which is reflected by the half-silvered mirror 3. Half-silvered mirror is here used generically to refer to any device which is suitable for splitting the light beam into two portions, one of which is reflected by a plane mirror 4. The beam thus reflected is formed into a parallel scanning beam by means of a polygonal rotary mirror 5 and a convex lens 8. The parallel scanning beam thus formed is used to scan the surface of the object for inspection. The laser beam after it has scanned the object passes to a convex lens 11 where it is collected and applied to a light receiving unit 12. The light receiving unit 12 is a photomultiplier in which variations in the intensity of light caused by variations in thickness of the object 9 and by variations in the evenness of the surface thereof are converted into an electrical signal which is suitably amplified.

The half-silvered mirror 3 is disposed so as to reflect a portion of the laser beam along the path indicated by broken lines to the scanning mirror 5 and then, as the scanning mirror rotates, towards phototransistors 6 and 7 at two rotational angles for each mirror facet so that the beam scanning period is detected by the phototransistors 6 and 7. Phototransistors 6 and 7 are disposed in a plane other than the plane in which the scanning of the inspecting beam is carried out. Synchronizing pulses are formed from the output signals from phototransistors 6 and 7 by a flip-flop circuit of well-known construction. The output signal from the light receiving unit 12 and a reference voltage are compared in a voltage comparator circuit. In this circuit, the output signal from the light receiving unit 12 is gated in accordance with the synchronizing pulses in only the range necessary for the inspection. As a result of the comparison, output signals which exceed a pre-set level are applied to a check circuit such as a warning signal generator circuit or a recording display circuit.

Figure 2:
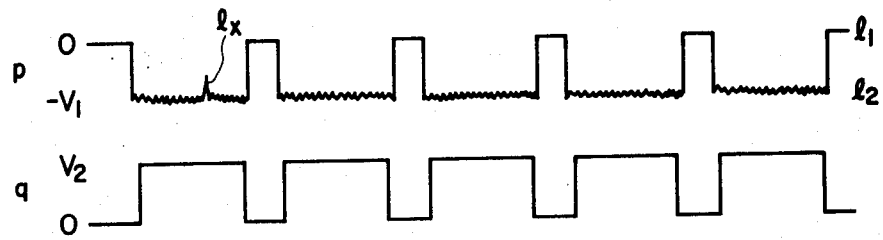
FIG. 2 is a graph showing certain signals in the embodiment of FIG. 1.

The above-described operation will become more apparent from FIG. 2, in which reference character p designates the scanning signal, q the synchronizing pulse, $l_1$ a blank level where the output signal is gated off by the synchronizing pulses, and $l_2$ the signal level. In FIG. 2, the peak ($l_x$) of the signal level $l_2$ at the left-hand side of the figure indicates that foreign material has been detected.

In the above-described embodiment, a laser beam is most suitable as the light source for precision inspection. However, depending on the amount of accuracy required, a xenon lamp or other ordinary light sources may be employed. In addition, instead of the polygonal rotary mirror 5, a vibrating mirror may be used.

The section of the inspecting pencil of light beam may be circular. However, in order to improve the sensitivity of the apparatus, it is preferable that the section is rectangular or elliptical in which the height is smaller than the width so that the percentage of variations of the light intensity with respect to variations of the height of an object under inspection is maximized.

Figure 3:
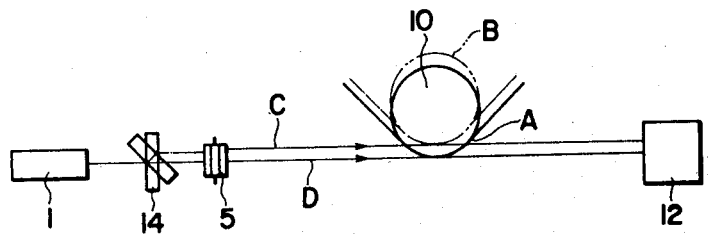
FIG. 3 is a side view showing the displacement of a conveying roll.

Should higher accuracy be required, it is necessary to allow the laser beam scanning the surface of an object being inspected to automatically follow the surface of the object by tracking the surface of the object, for example, in a relationship such that the light amplitude is decreased by 10%. Such an embodiment can be implemented as shown in FIG. 3 in which means is provided for causing the light beam path to follow the surface of the object by changing the angle of inclination of a plane-parallel transparent plate 14 disposed between the half-silvered mirror 3 and the plane mirror 4. The means which causes the light beam path to follow the surface of the object is referred to herein as "a beam shifter."

Figure 5:
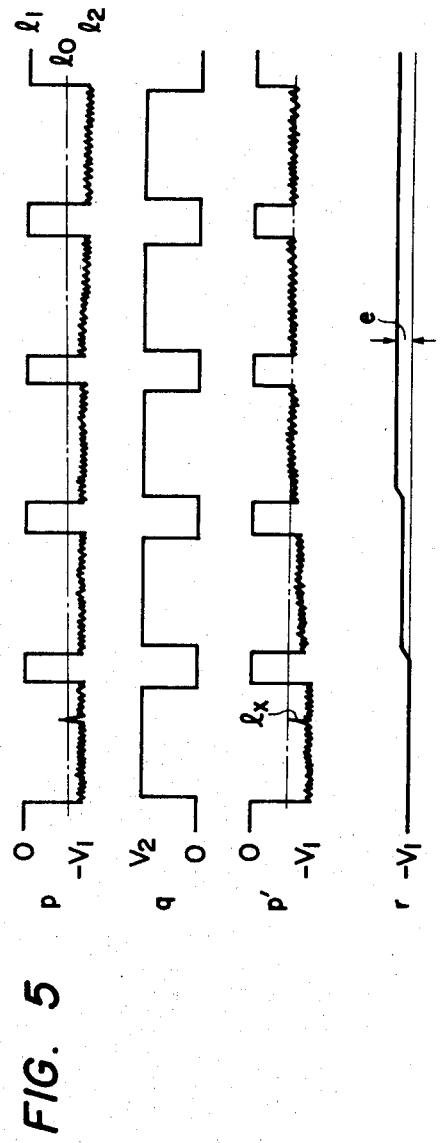
FIG. 5 is a graph showing signals in the embodiment of FIG. 4.

The principle of operation of the beam shifter and a preferred method of control thereof will be described with reference to the embodiment shown in FIG. 3. It is assumed that when the conveying roll is in a position B as shown in FIG. 3, the scanning beam scans along path C. In this case, the output inspection signal from the receiving unit 12 is as indicated by the signal as shown in FIG. 5. In the diagram, reference character $l_0$ designates the detection level. If, under this condition, the position of the conveying roll were changed to a position A by an external factor such as for instance variation of the tension applied to the object being inspected and the scanning beam path were maintained along path C, the inspection accuracy would decrease. In fact, if the movement of the conveying roll with respect to the scanning beam is large, it is impossible to carry out the inspection. In this case, the inspection signal would be as indicated by signal P' in FIG. 5. The frequency components of an output inspection signal which is produced by variations in the roughness of the surface of an object being inspection are typically more than 200 times as high as the frequency components of the output inspection signal produced by displacement of the conveying roll. The beam shifter makes it possible to correct such displacement by changing beam path C into beam path D with the inclination of the plate 14 of FIG. 3. Signal P' in FIG. 5 is an example of an output inspection signal containing such variations which, upon filtering, to remove the high frequency components appear as signal r indicative of only the displacement of roll 10.

Figure 4:
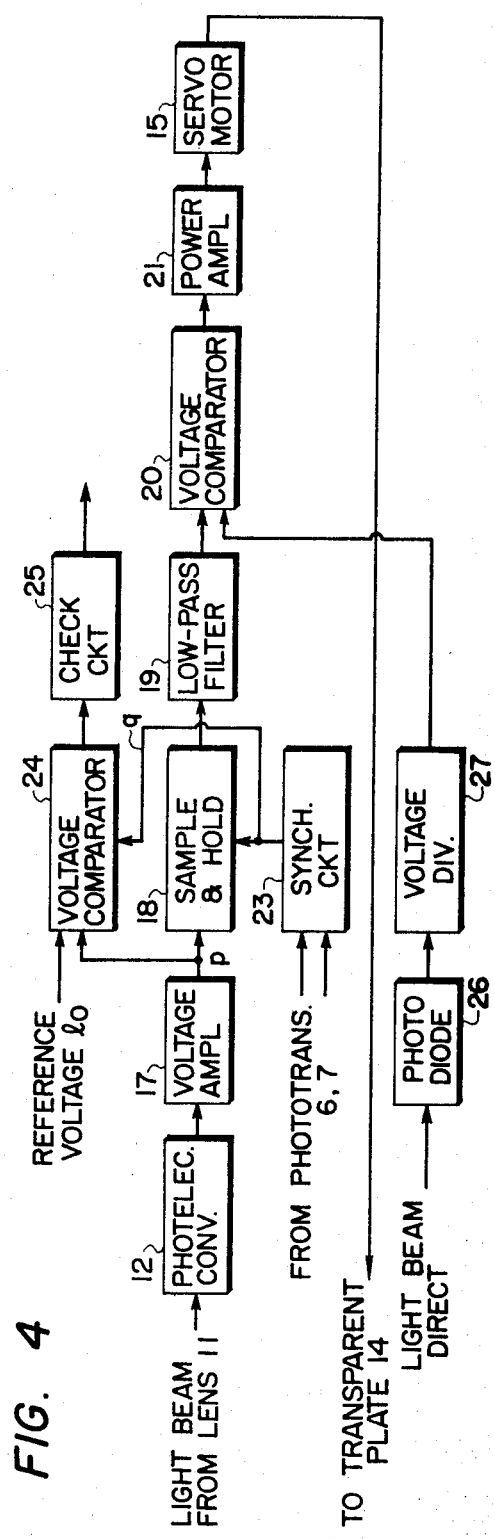
FIG. 4 is a block diagram of a second embodiment of the invention.

An example of a circuit capable of separating out the low frequency components and correcting the output inspection signal is shown in FIG. 4. This circuit includes a photoelectric converter 16 which forms a part of the light receiving unit 12 of FIG. 1, a voltage amplifier 17, a sample-and-hold circuit 18, a low-pass filter 19, a voltage comparator of difference circuit 20, a power amplifier 21, a beam shifter drive circuit 22, a synchronization circuit 23, a voltage comparator 24, check circuit 25, a light quantity measuring unit implemented as a photodiode 26, and a variable voltage divider 27. With the angle of inclination of the plate 14 of FIG. 3 controlled by the servomotor 15 so that the voltage component of the output inspection signal caused by displacement of the conveying roll is held at zero by operation of this circuit, the scanning beam will properly follow the displacement of the conveying roll at all times.

The power of the laser beam may be expected to vary with time. Therefore, in accordance with one aspect of the invention, a portion of the laser beam is branched by the half-silvered mirror directly to the light quantity measuring unit 26 so that the power of the laser beam is measured by the light quantity measuring unit 26. The output voltage from the light quantity measuring unit 26 is divided by the variable voltage divider 27 so that a certain percentage, for instance 10%, of the light quantity of the scanning laser beam is used as the comparison voltage for the voltage comparator 20. With this arrangement, because a portion of the original beam, rather than an independent fixed reference source, is used to generate a reference signal, even if the power of the laser varies, the circuit will nonetheless cause the laser beam to follow the surface of the object.

As the device of the invention operates by optical means even if the type of object to be inspected is varied, the device can be readily re-adjusted to operate with the new object type. Moreoover, even if the measurement surface of an object being inspected is vertically moved by some tension which may be applied thereto or by an increase in the diameter of the conveying roll, such as may be attributed to an increase in temperature thereof during conveyance of the object, the inspection can still be carried out with a high accuracy.

As is believed evident, it is necessary to change the parallel speed of the scanning light beam in the width direction in proportion to increases and decreases in the speed of the object in order to maintain the same accuracy. In addition, it is obvious that the inspection accuracy can be improved by increasing the scanning density of the light beam.

What is claimed is:

1. A device for continuously inspecting a surface comprising: a cylindrical roll for bending and conveying an object to be inspected, means for emitting a light beam in a direction substantially tangential to an outer surface of said object on said cylindrical roll, means for scanning said light beam in the widthwise direction of said object, means for receiving said light beam for producing an output signal in response thereto, means for comparing said output signal with a reference signal, a plane-parallel, transparent plate disposed in the path of said light beam prior to said surface, and means for varying an angle of inclination of said plate disposed in said light beam so that said light beam path is caused to follow variations in position of said surface of said object.

2. The inspection device of claim 1 wherein said light beam emitting means comprises a laser light source.

3. A device for continuously inspecting a surface of a belt-like article comprising:
a cylindrical roll for conveying a belt-like article, said article being bent around at least a portion of an outer surface of said roll;
means for providing a beam of light;
means for scanning said light beam;
half-silvered mirror means disposed in the path of said light beam, a first portion of said light beam being reflected from said half-silvered mirror means directly to said scanning means and a second portion of said light beam passing through said half-silvered mirror means;
reflecting mirror means disposed to reflect said second portion of said light beam to said scanning means;
first and second light detecting means; said half silvered mirror means, said reflecting mirror means, said scanning means and said first and second detector means being disposed such that said first portion of said light beam is scanned in a plane containing said first and second detecting means and such that said second portion of said light beam is scanned in a different plane substantially tangent to an outer surface of said object on said roll;
means for receiving at least portions of the beam scanned on said object for producing an electrical signal in response thereto and indicative of the smoothness of said surface;
means for producing a synchronizing signal in response to output signals from said first and second light detecting means;
means for sampling and holding said electrical signal produced in response to said scanned beam;
means, gated by said synchronizing signal, for comparing said electrical signal with a reference voltage; low-pass filter means for filtering an output signal from said sampling and holding means;
means for comparing an output signal from said low-pass filter means with a reference signal indicative of the path of said second portion of said light beam on said surface; and
means for varying the path of said second portion of said light beam in response to an output signal from said comparing means to maintain said second light beam portion tangential to said surface.

4. The inspecting device as claimed in claim 3 wherein said means for providing a beam of light comprises a laser light source.

5. The inspecting device as claimed in claim 1 wherein said scanning means comprises a multi-faced rotating mirror.

6. The inspecting device as claimed in claim 3 wherein said receiving means comprises a convex lens and a light sensitive semiconductor device.

7. The inspecting device as claimed in claim 3 wherein said light beam path varying means comprises beam shifter means, and a servo motor mechanically operatively coupled thereto.

8. The inspecting device as claimed in claim 7 wherein said comparing means comprises a difference forming circuit.

9. The inspecting device as claimed in claim 3 further comprising means for producing said reference signal in response to the intensity of said light beam.

* * * * *